United States Patent
Solar

(10) Patent No.: US 6,254,608 B1
(45) Date of Patent: Jul. 3, 2001

(54) SHEATHLESS DELIVERY CATHETER FOR RADIALLY EXPANDABLE INTRALUMINAL STENTS AND STENTED GRAFTS

(75) Inventor: Ronald J. Solar, 12495 Figtree St., San Diego, CA (US) 92131

(73) Assignee: Ronald J. Solar, San Diego, CA (US)

( * ) Notice: Subject to any disclaimer, the term of this patent is extended or adjusted under 35 U.S.C. 154(b) by 0 days.

(21) Appl. No.: 08/918,621

(22) Filed: Aug. 22, 1997

(51) Int. Cl.[7] .................................................. A61F 11/00
(52) U.S. Cl. ......................... 606/108; 606/194; 606/195
(58) Field of Search .................................. 606/108, 198, 606/194, 195, 153; 604/96, 53, 101, 104, 194, 11, 14, 52; 623/2, 12

(56) References Cited

U.S. PATENT DOCUMENTS

| | | | |
|---|---|---|---|
| 5,026,377 | * 6/1991 | Burton et al. ........................ | 606/108 |
| 5,290,306 | * 3/1994 | Trotta et al. ......................... | 606/194 |
| 5,372,600 | * 12/1994 | Beyar et al. ......................... | 606/108 |
| 5,447,497 | * 9/1995 | Sogard et al. ....................... | 604/101 |
| 5,484,449 | * 1/1996 | Amundson et al. ................. | 606/108 |

* cited by examiner

Primary Examiner—Michael Buiz
Assistant Examiner—Lien Ngo
(74) Attorney, Agent, or Firm—Robert D. Buyan; Stout, Uxa, Buyan & Mullins, LLP

(57) ABSTRACT

A delivery catheter for a radially expandable intraluminal stent or stented graft. The delivery catheter comprises an elongate catheter body defining proximal and distal ends and at least one lumen extending longitudinally therethrough. Disposed on the catheter body at a location proximal to the distal end thereof is an inflatable, expandable balloon. The balloon is at least partially fabricated from a conformable material for allowing the stent to be at least partially embedded therein when positioned thereupon.

29 Claims, 2 Drawing Sheets

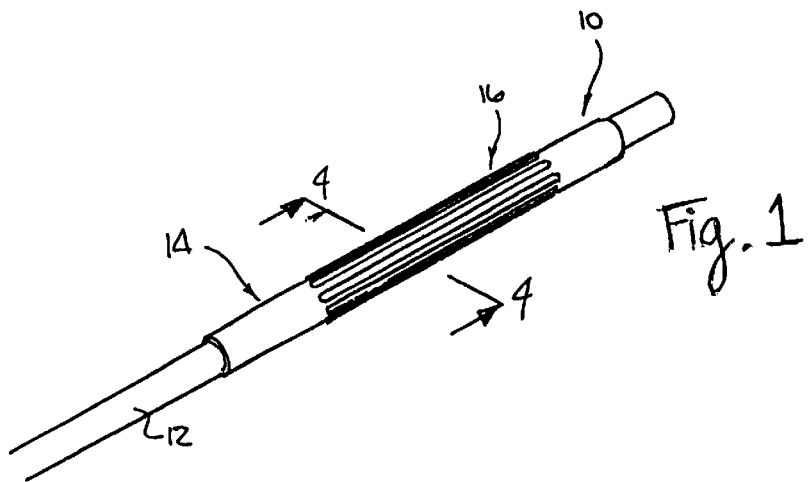
Fig. 1
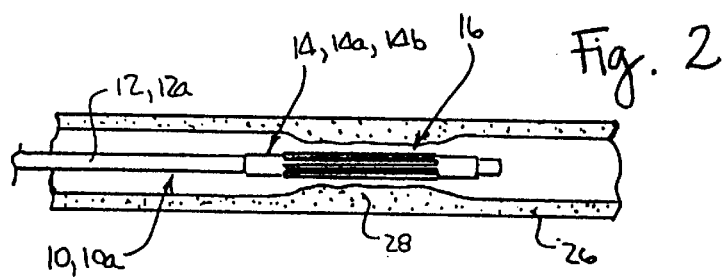
Fig. 2
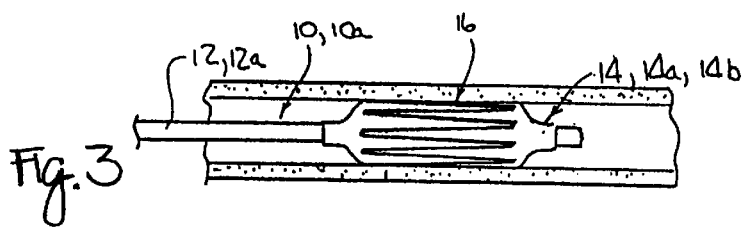
Fig. 3
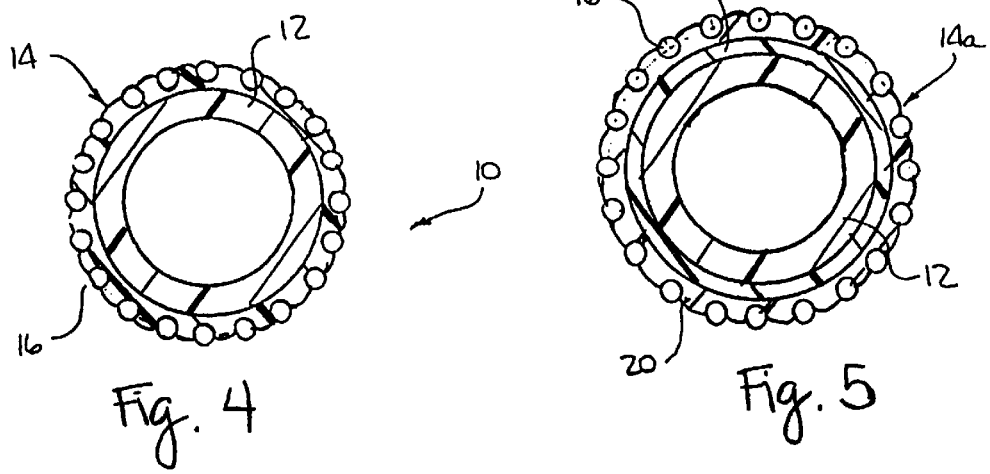
Fig. 4
Fig. 5

SHEATHLESS DELIVERY CATHETER FOR RADIALLY EXPANDABLE INTRALUMINAL STENTS AND STENTED GRAFTS

FIELD OF THE INVENTION

The present invention pertains generally to medical devices, and more particularly to a delivery system for a radially expandable intraluminal stent device. In accordance with one embodiment of the present invention, a pressure expandable stent is held upon an inflatable balloon which is used to facilitate the radial expansion of the stent. The stent is held upon the balloon in a manner wherein slippage or movement of the stent is prevented during the navigation of a delivery catheter of the present delivery system to a desired treatment site. Additionally, the luminal surface of the anatomical passageway into which the delivery catheter is introduced is protected from damage or other injury during the advancement of the stent to the desired treatment site. These attributes of the present invention are achieved without the use of or need for an outer sheath which covers the stent during the intraluminal advancement thereof.

BACKGROUND OF THE INVENTION

The term "stent" is generally used to describe endoprothstetic medical devices which are implanted in anatomical passageways (e.g., blood vessels, gastrointestinal tract, genitourinary tract, endocrine ducts, etc . . . ) of the body for the purpose of maintaining the patency or state of dilation of the passageway, reinforcing the passageway, or anchoring a tubular graft or other object within the passageway.

Typically, such stents are implanted in blood vessels to maintain dilation and patency of an occluded region of blood vessel, or to bridge a weakened or aneurysmic region of blood vessel. On the other hand, some typical nonvascular applications of such stents are for the treatment of constrictions or injuries to the gastrointestinal tract (e.g., esophagus), ducts of the biliary tree (e.g., common bile duct) or anatomical passageways of the genitourinary tract (e.g., ureter, urethra fallopian tube, etc.).

Transluminally implantable stents are initially disposed in a compact configuration of relatively small diameter, and are initially mounted upon or within a delivery catheter to facilitate insertion and transluminal advancement of the stent into the desired anatomical passageway. Thereafter, such stents are radially expanded to a larger "operative" diameter which is equal to or slightly larger than the diameter of the anatomical passageway in which the stent is to be implanted. When radially expanded to such operative diameter, the stent will typically become released or separated from the delivery catheter and anchored or frictionally engaged to the surrounding wall of the anatomical passageway.

Some stents have a pliable, continuous tubular covering, in which case they are typically referred to as a "stented graft" or "stent-graft".

In general, stents and stented grafts fall into two major categories—a) self-expanding and b) pressure-expandable. Those of the self-expanding variety may be formed of resilient or shape memory material (e.g., spring steel or nitinol™) which is capable of self-expanding from its first (radially compact) diameter to its second (operative) diameter without the exertion of outwardly-directed force against the stent or stented graft. Examples of such self-expanding stents and stented grafts are set forth in U.S. Pat. No. 4,655,771 (Wallsten, et al); U.S. Pat. No. 4,954,126 (Wallsten); U.S. Pat. No. 5,061,275 (Wallsten, et al); U.S. Pat. No. 4,580,568 (Gianturco); U.S. Pat. No. 4,830,003 (Wolf, et al); U.S. Pat. No. 5,035,706 (Gianturco, et al); U.S. Pat. No. 5,330,400 (Song) and U.S. Pat. No. 5,354,308 (Simon, et al) and Foreign Patent Publication Nos. WO94\12136; WO92\06734 and EPA183372. Those of the pressure-expandable (i.e., "passive expandable") variety may be formed of plastically deformable material (e.g., stainless steel) which is initially formed in its first (radially compact) diameter and remains stable in such first diameter until such time outwardly directed pressure is exerted upon the stent or stented graft to cause radial expansion and resultant plastic deformation of the stent or stented graft, to its second (operative) diameter. Examples of such pressure-expandable stents and stented grafts are set forth in U.S. Pat. No. 5,135,536 (Hillstead); U.S. Pat. No. 5,161,547 (Tower); U.S. Pat. No. 5,292,331 (Boneau); U.S. Pat. No. 5,304,200 (Spaulding); U.S. Pat. No. 4,733,665 (Palmaz); U.S. Pat. No. 5,282,823 (Schwartz, et al); U.S. Pat. No. 4,776,337 (Palmaz); and U.S. Pat. No. 5,403,341 (Solar) and Foreign Patent Publication Nos. EPA480667; and WO95\08966.

In many applications, careful positioning and sound anchoring of the stent or stented graft is critical to the successful treatment of the underlying medical problem. In this regard, the delivery catheter which is utilized to insert and position the stent or stented graft may be an important aspect of the overall system. Various types of delivery catheters for stents and stented grafts have been previously known, including those described in U.S. Pat. No. 4,665,918 (Garza, et al); U.S. Pat. No. 4,733,665 (Palmaz); U.S. Pat. No. 4,739,762 (Palmaz); U.S. Pat. No. 4,762,125 (Leiman, et al);, U.S. Pat. No. 776,337 (Palmaz); U.S. Pat. No. 4,838,269 (Robinson, et al); U.S. Pat. No. 4,994,071 (MacGregor); U.S. Pat. No. 5,037,427 (Harada, et al); U.S. Pat. No. 5,089,005 (Harada); U.S. Pat. No. 5,102,417 (Palmaz); U.S. Pat. No. 5,108,416 (Ryan, et al); U.S. Pat. No. 5,141,498 (Christian); U.S. Pat. No. 5,181,920 (Mueller, et al); U.S. Pat. No. 5,195,984 (Schatz); U.S. Pat. No. 5,201,901 (Harada, et al); U.S. Pat. No. 5,269,763 (Boehmer, et al); U.S. Pat. No. 5,275,622 (Lazarus, et al); U.S. Pat. No. 5,290,295 (Querals, et al); U.S. Pat. No. 5,306,294 (Winston, et al); U.S. Pat. No. 5,318,588 (Horzewski, et al); U.S. Pat. No. 5,344,426 (Lau, et al); U.S. Pat. No. 5,350,363 (Goode, et al); U.S. Pat. No. 5,360,401 (Turnland); U.S. Pat. No. 5,391,172 (Williams, et al); U.S. Pat. No. 5,397,345 (Lazarus); U.S. Pat. No. 5,405,380 (Gianotti, et al); U.S. Pat. No. 5,443,452 (Hart, et al); U.S. Pat. No. 5,453,090 (Martinez, et al); U.S. Pat. No. 5,456,284 (Ryan, et al); and U.S. Pat. No. 5,456,694 (Marin, et al) and Foreign Patent Publication Nos. EP-0308-815-A2; EP-0335341-A1; EP-364-787-A; EP-0442-657-A2; EP-482976-A; EP-0505686-A1; EP-0611-556-A1; EP-0638-290-A1; WO94\15549;

WO95\01761; GB2196-857-A; DE3042-229; and DE3737-121-A.

As previously indicated, many types of stents or stented grafts are currently used in relation to the treatment of various disorders. Perhaps the most common use of stents and stented grafts is in relation to the treatment of narrowed or constricted blood vessels. For these applications, pressure expandable stents are typically employed, with the delivery of the stent to the desired treatment site being facilitated through the use of a delivery catheter including an inflatable balloon which is used to facilitate the radial expansion of the stent positioned thereupon to its final, operative diameter.

In this particular application, two serious problems are known to often occur during the advancement of the stent through the anatomical passageway (e.g., the blood vessel).

These problems include the tendency of the stent to slip off of the balloon of the delivery catheter, and occurrences of the stent scraping or otherwise damaging the lining of the anatomical passageway through which the delivery catheter is advanced. Slippage of the stent upon the balloon of the delivery catheter may result in improper placement of the stent within the treatment site, thus requiring the use of additional stents to correct such improper placement. More seriously, such slippage may cause the stent to be "lost", thus giving rise to the risk of the stent embolizing in its unexpanded state. The scraping of the lining of the anatomical passageway (e.g., the intima of an artery) may lead to complications such as spasm, thrombosis and/or perforation of the passageway.

In an attempt to solve these particular problems, delivery catheters constructed in accordance with the prior art often employ sheaths of various designs which are used to cover the stent positioned upon the furled balloon during the advancement of the delivery catheter through the anatomical passageway. In other prior art designs, the stent is mounted over a balloon which is attached to an inner tube, with the inner tube itself residing within an outer tube which acts as a sleeve or sheath. However, these prior art designs which incorporate sheaths or outer tubes which act as sheaths add significant bulk to the delivery catheter, and increase the size and stiffness of the delivery system. Such increased rigidity causes difficulties in navigating the delivery catheter through tortuous anatomical passageways, and thus may interfere with the safe placement of the stent into the desired treatment site. Additionally, in those prior art systems employing an outer tube which acts as a sheath, the outer tube itself creates a surface upon which the end of the stent can inadvertently catch, with the inclusion of the outer tube also making it difficult to determine when the same has been completely retracted or withdrawn from the stent. In this respect, the inclusion of the outer tube creates a manipulative problem regarding whether the stent has been sufficiently exposed prior to its radial expansion. Additionally, the readvancement of the outer tube over the stent is difficult if the stent must be repositioned within the anatomical passageway. Moreover, the inclusion of sheaths or outer tubes in the prior art delivery systems adds costs thereto, and further increases the complexity of the stent placement procedure. The present invention overcomes these prior art deficiencies by providing a delivery system for a stent or stented graft which prevents the stent from slipping and protects the anatomical passageway during stent placement without having the bulk of a sheath or other stent coverings such as an outer tube.

SUMMARY OF THE INVENTION

In accordance with a first embodiment of the present invention, there is provided a delivery catheter for a radially expandable intraluminal stent or stented graft. The delivery catheter comprises an elongate catheter body which defines proximal and distal ends and at least one lumen extending longitudinally therethrough. Disposed on the catheter body at a location proximal to the distal end thereof is an inflatable, expandable balloon. The balloon is at least partially fabricated from a conformable material for allowing the stent to be at least partially embedded therein when positioned thereupon. The term conformable, as used herein and as shown in the accompanying drawings, refers to a substance that is flowable or compressible such that a) the substance may be indented when pressure is exerted upon it by an object such as a radially collapsed stent and b) the object, such as a radially collapsed stent, can become nested within such indentation(s) and thereby at least partially embedded within said conformable material.

In the first embodiment of the present invention, the balloon may be completely fabricated from the conformable material which is selected from the group consisting of polyethylene (PE), polyurethane (PU), silicone rubber, and nylon. The polyethylene which may serve as the conformable material is preferably low density polyethylene (LDPE) with the nylon being PEBAX™ (Atochimie, Courbevoie, Hauts-Ve-Sine, France). In addition to being completely fabricated from the conformable material, the balloon has a preferred wall thickness of about 0.001 to 0.005 inches.

Rather than being completely fabricated from the conformable material, the balloon of the delivery catheter constructed in accordance with the first embodiment may alternatively comprise an inner layer which is fabricated from a non-compliant material, and an outer layer which is fabricated from a conformable material, with the stent being at least partially embedded in the outer layer of the balloon when positioned thereupon. The conformable material for the outer layer of the balloon is preferably selected from the previously described group of conformable materials, with the non-compliant material for the inner layer of the balloon preferably being selected from the group consisting of polyethylene, polyethylene terephthalate (PET), nylon and combinations thereof. The polyethylene which may be used for the non-compliant material is preferably high-density polyethylene (HDPE). When the balloon comprises the inner and outer layers, the inner layer has a preferred thickness of about 0.0001 to 0.0015 inches, with the outer layer having a preferred thickness of about 0.0009 to 0.0035 inches. Additionally, the balloon may be fabricated via a co-extrusion process to define the inner and outer layers, or may include an outer balloon which defines the outer layer and an inner balloon which is disposed within the outer balloon and defines the inner layer.

The delivery catheter constructed in accordance with the first embodiment of the present invention is preferably used in combination with a pressure-expandable stent which is positioned upon the inflatable balloon. However, the delivery catheter 10 of the first embodiment may also be used in combination with any stent which may be radially expanded by outward radial pressure (e.g., a ratcheting stent). Additionally, the catheter body preferably defines at least two (2) lumens, including a balloon inflation lumen and a guidewire lumen.

In accordance with a second embodiment of the present invention, there is provided a delivery catheter for a radially expandable intraluminal stent, with the delivery catheter comprising an elongate catheter body defining proximal and distal ends and at least one lumen extending longitudinally therethrough. Disposed on the catheter body at a location proximal to the distal end thereof is an inflatable, expandable balloon. Additionally, disposed on the balloon is a conformable element, with the stent being at least partially embedded in the conformable element when positioned thereupon.

In the second embodiment of the present invention, the conformable element may comprise a coating of a conformable material which is applied to the balloon at a preferred thickness of from about 0.001 to 0.005 inches. The conformable material for the coating may be selected from the group of materials consisting of wax, silicone rubber, plastic foam, polyurethane, and natural or synthetic rubber. As an alternative to the coating, the conformable element may comprises a sleeve positioned on the balloon, with the sleeve having a preferred wall thickness of about 0.002 to 0.005.

The sleeve itself is preferably fabricated from a conformable material, examples of which include polymeric materials and elastomeric or flexible materials. Like the delivery catheter constructed in accordance with the first embodiment, the delivery catheter of the second embodiment is preferably used in combination with a pressure-expandable vascular stent positioned on the conformable element, with the catheter body itself defining a balloon inflation lumen and a guidewire lumen. In accordance with a third embodiment of the present invention, there is provided a delivery catheter for a radially expandable intraluminal stent, with the delivery catheter comprising an elongate catheter body defining proximal and distal ends and at least one lumen extending longitudinally therethrough. Disposed on the catheter body at a location proximal to the distal end thereof is a conformable element. The conformable element is at least partially fabricated from a conformable material for allowing the stent to be at least partially embedded therein when positioned thereupon.

In the third embodiment, the conformable element may comprise a coating of a conformable material which is applied to the catheter body, and is preferably selected from the group of materials consisting of wax, silicone rubber, polyurethane, plastic foam, and natural or synthetic rubber. The coating is preferably applied to the catheter body at a thickness from about 0.001 to 0.005 inches. The conformable element may alternatively comprise a sleeve positioned on the catheter body, with the sleeve having a preferred wall thickness of from about 0.002 to 0.005 inches and being fabricated from a conformable material, examples of which include polymeric materials and elastomeric or flexible materials. The delivery catheter of the third embodiment is preferably used in combination with a self-expanding vascular stent positioned on the conformable element, with the catheter body defining a guidewire lumen and, optionally, a secondary lumen for administering a drug.

Further in accordance with the present invention, there is provided a method of delivering a radially expandable intraluminal stent to a desired intraluminal site. The method comprises the initial step providing a delivery catheter which has the structural elements or attributes of the delivery catheter constructed in accordance with one of the three previously described embodiments of the present invention. If the delivery catheter includes an inflatable balloon, the method includes the further step of positioning a pressure-expandable vascular stent on the balloon itself or upon the conformable element disposed on the balloon such that the stent is at least partially embedded in the balloon or the conformable element thereupon. Thereafter, the catheter body is advanced over a guidewire until such time as the balloon with or without the conformable element is positioned within the desired intraluminal site. The balloon is then inflated so as to facilitate the radial expansion of the stent alone or in combination with the conformable element. The balloon may be inflated with either a liquid or a gas.

In the event the delivery catheter does not incorporate the inflatable balloon, the method comprises the further step of positioning a self-expanding stent on the conformable element of the delivery catheter such that the stent is at least partially embedded therein. The catheter body is then advanced over a guidewire until such time as the conformable element is positioned within the desired intraluminal site. Thereafter, the self-expanding stent which is positioned upon the conformable element is radially expanded to its operative diameter within the treatment site.

As previously indicated, in those embodiments of the present delivery system wherein the delivery catheter incorporates an inflatable balloon, the balloon itself is fabricated from a conformable material, or has a conformable element or coating disposed thereon such that when the balloon is in its folded or furled configuration and a stent or stented graft is crimped or otherwise compressed onto the furled balloon, the stent will be embedded within the balloon or the conformable element or coating thereupon. Depending upon the particular design of the stent or stented graft, such embedding may be partial or complete. As also previously indicated, the catheter body defines at least one lumen which allows for gas or liquid to pass to the balloon (if included in the delivery catheter) to facilitate the radial expansion of the balloon and hence the stent positioned thereupon. The catheter body preferably includes an additional lumen which may be used for guidewire passage, drug delivery, etc. Those of ordinary skill in the art will recognize that the catheter body may be of a concentric or multi-lumen design, and may be of the over-the-wire type or rapid-exchange or "monorail" type.

As also previously indicated, the delivery system of the present invention is typically used in conjunction with stents or stented grafts, with usable stents including tube type stents and coil type stents. Additionally, the present delivery system is usable in relation to non-balloon, self-expanding stents, with such stents being fully or partially embedded in a conformable element which is not radially expanded during the deployment of the stent into the treatment site.

BRIEF DESCRIPTION OF THE DRAWINGS

These, as well as other features of the present invention, will become more apparent upon reference to the drawings wherein:

FIG. 1 is a partial perspective view of a delivery catheter constructed in accordance with a first embodiment of the present invention having a pressure expandable stent positioned thereupon;

FIG. 2 is a cross-sectional view illustrating the manner in which the delivery catheter and accompanying stent shown in FIG. 1 are positioned relative to a desired treatment site within an anatomical passageway;

FIG. 3 is a cross-sectional view illustrating the manner in which the balloon of the delivery catheter shown in FIGS. 1 and 2 is inflated to facilitate the radial expansion of the stent into engagement with the luminal surface of the anatomical passageway at the treatment site;

FIG. 4 is a cross-sectional view taken along line 4—4 of FIG. 1 illustrating a first embodiment of the balloon of the delivery catheter;

FIG. 5 is a cross-sectional view similar to FIG. 4 illustrating a second embodiment of the balloon of the delivery catheter;

DETAILED DESCRIPTION OF THE PREFERRED EMBODIMENTS

Figure 6:
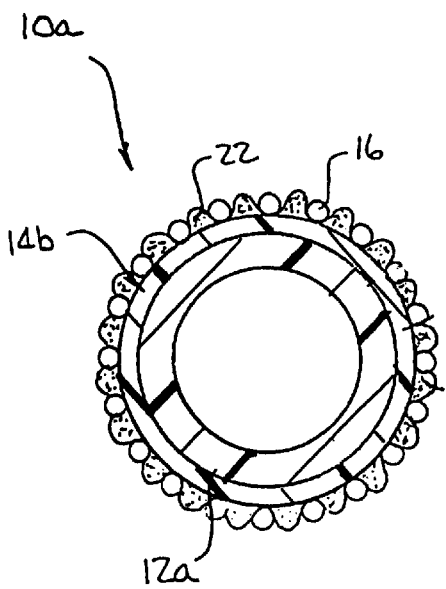
FIG. 6 is a cross-sectional view of a delivery catheter constructed in accordance with a second embodiment of the present invention illustrating a first embodiment of a conformable element disposed upon the balloon of the delivery catheter.

Referring now to the drawings wherein the showings are for purposes of illustrating preferred embodiments of the present invention only, and not for purposes of limiting the same, FIG. 1 shows a delivery catheter 10 constructed in accordance with a first embodiment of the present invention. The delivery catheter 10 is of the type typically referred to as a "balloon delivery catheter", and comprises an elongate, tubular catheter body 12 having an inflatable balloon 14 attached to the outer surface thereof at a location proximal to the distal end of the catheter body 12. The catheter body 12 preferably defines both a balloon inflation lumen and a guidewire lumen. The delivery catheter 10 of the present invention is used in conjunction with a radially expandable stent or stented graft, and in particular a pressure expandable stent 16 or stented graft. The pressure expandable stent 16 shown in FIGS. 1–7 is typically referred to as a "zig-zag" stent, though it will be recognized by those of ordinary skill in the art that the delivery catheter 10 constructed in accordance with the first embodiment of the present invention may also be used in conjunction with alternative types of pressure expandable stents or stented grafts.

The stent 16 or stented graft is mounted to the balloon 14 of the delivery catheter 10. In this respect, such mounting is typically facilitated by radially collapsing or compressing the stent 16 about the balloon 14. The size of the balloon 14 relative to the size of the stent 16 is such that when the stent 16 is centrally positioned on the balloon 14 and mounted thereto in the aforementioned manner, the opposed ends of the balloon 14 will protrude from respective ends of the stent 16. As will be described in more detail below, the balloon 14 is at least partially fabricated from a conformable material, or includes a conformable coating or sleeve applied thereto, for allowing the stent 16 to be at least partially embedded within the delivery catheter 10.

Referring now to FIGS. 1 and 4, in the delivery catheter 10 constructed in accordance with the first embodiment of the present invention, the balloon 14 may be completely fabricated from a conformable material which is selected from the group consisting of polyethylene (PE), polyurethane (PU), silicone, rubber, and nylon. The polyethylene which may serve as the conformable material is preferably low-density polyethylene (LDPE), with the nylon being PEBAX™ (Atochimie, Courbevoie, Hauts-Ve-Sine France). The balloon 14 has a preferred wall thickness of about 0.001 to 0.005 inches. Because the balloon 14 is completely fabricated from the conformable material, the stent 16 is at least partially embedded therein when radially compressed thereabout. Though, as shown in FIG. 4, the stent 16 is only partially embedded within the balloon 14, it will be recognized that the thickness of the balloon 14 may be such that the stent 16 is completely embedded therein.

Referring now to FIGS. 1 and 5, the delivery catheter 10 of the first embodiment may alternatively be provided with a balloon 14a which, rather than being completely fabricated from a conformable material, comprises an inner layer 18 which is fabricated from a non-compliant material and an outer layer 20 which is fabricated from a conformable material. In this respect, the stent 16 is radially compressed about the outer layer 20 of the balloon 14a and at least partially embedded therein. The conformable material for the outer layer 20 of the balloon 14a is preferably selected from the previously described group of conformable materials used for the balloon 14, with the non-compliant material for the inner layer 18 of the balloon 14a preferably being selected from the group consisting of polyethylene, polyethylene terephthalate (PET), nylon and combinations thereof. The polyethylene which may be used for the non-compliant material is preferably high-density polyethylene (HDPE). When the balloon 14a comprises the inner and outer layers 18, 20, the inner layer 18 has a preferred thickness of about 0.0001 to 0.0015 inches, with the outer layer 20 having a preferred thickness of about 0.0009 to 0.0035 inches. The balloon 14a may be fabricated via a co-extrusion process to define the inner and outer layers 18, 20, or may include an outer balloon which defines the outer layer 20 and a separate inner balloon which is disposed within the outer balloon and defines the inner layer 18.

Referring now to FIGS. 1 and 6, in accordance with a second embodiment of the present invention there is provided a delivery catheter 10a which is substantially identical in construction to the previously described delivery catheter 10, but is alternatively provided with an inflatable balloon 14b upon the catheter body 12a which is not itself fabricated from a conformable material, and does not include an outer layer of conformable material. Rather, the balloon 14b is of conventional construction. However, in the delivery catheter 10a the balloon 14b includes a conformable element disposed thereon which may comprise a coating 22 of a conformable material. The coating 22 is applied to the balloon 14b, with the stent 16 being at least partially embedded in the coating 22 when radially compressed about the balloon 14b. As seen in FIG. 6, when the stent 16 is radially collapsed about the balloon 14b, the coating 22 flows upwardly between the adjacent segments of the stent 16, thus causing the stent 16 to be effectively embedded within the coating 22. The conformable material for the coating 22 is preferably selected from the group consisting of wax, silicone rubber, polyurethane, plastic foam, and natural or synthetic rubber.

Figure 7:
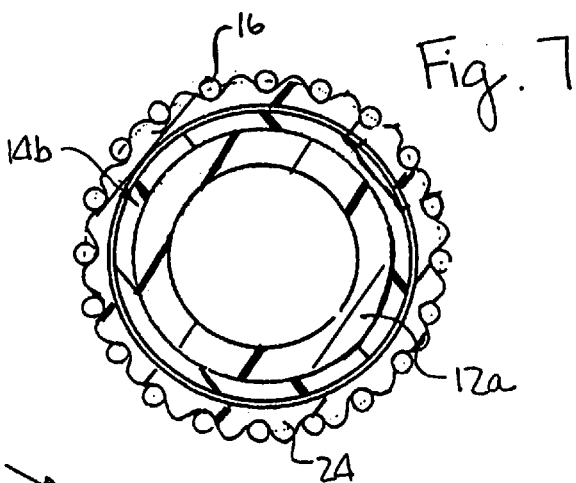
FIG. 7 is a cross-sectional view similar to FIG. 6 illustrating a second embodiment of the conformable element disposed upon the balloon of the delivery catheter.

Referring now to FIGS. 1 and 7, the delivery catheter 10a may be provided with a conformable element which, as an alternative to the previously described coating 22, comprises a separate sleeve 24 disposed upon the balloon 14b. The sleeve 24 is positioned upon the balloon 14b and is fabricated from a conformable material selected from the group consisting of polymeric and elastomeric materials. Additionally, the sleeve 24 has a preferred wall thickness of about 0.002 to 0.005 inches. As seen in FIG. 7, the stent 16 is at least partially embedded in the sleeve 24 when radially compressed or collapsed about the balloon 14b.

Referring now to FIGS. 2 and 3, in using the delivery catheter 10, 10a, the stent 16 is mounted thereto so as to be at least partially embedded within the balloon 14, 14a, coating 22 or sleeve 24. Thereafter, the delivery catheter 10, 10a is advanced through a anatomical passageway 26 to a desired treatment site 28 such as a narrowed or constricted opening within the passageway 26. More particularly, the catheter body 12, 12a is advanced through the treatment site 28 such that the stent 16 is operatively positioned therewithin. Thereafter, the balloon 14, 14a, 14b is pressurized with a gas or fluid, thus resulting in the radial expansion of the stent 16 into direct engagement of with the luminal surface of the anatomical passageway 26 at the treatment site 28. Importantly, since the stent 16 is at least partially embedded in the balloon 14, 14a or in the coating 22 or sleeve 24 applied to the balloon 14b, the stent 16 is prevented from moving or slipping along the catheter body 12, 12a during the advancement thereof, and is further prevented from damaging or interfering with the luminal surface of the anatomical passageway 26.

Figure 8:
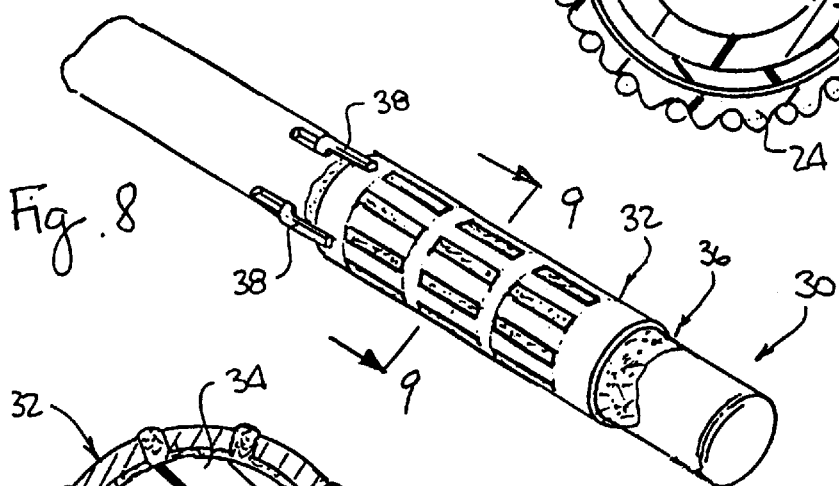
FIG. 8 is partial perspective view of a delivery catheter constructed in accordance with a third embodiment of the present invention including a self expanding stent positioned thereupon.
Figure 9:
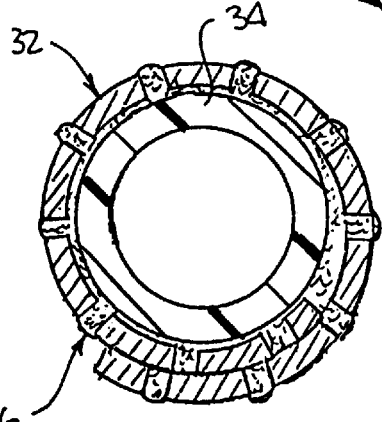
FIG. 9 is a cross-sectional view taken along line 9—9 of FIG. 8.

Referring now to FIGS. 8 and 9, there is depicted a delivery catheter 30 which is constructed in accordance with a third embodiment of the present invention and is specifically adapted to be used in conjunction with a self expanding stent 32 or stented graft as an alternative to the previously described pressure expandable stent 16. The delivery catheter 30 comprises an elongate, tubular catheter body 34. The catheter body 34 of the delivery catheter 30 defines a guidewire lumen, and may optionally include a secondary lumen for administering a drug. Attached to the outer surface of the catheter body 34 at a location proximal to the distal end thereof is a conformable element 36.

In the delivery catheter 30 constructed in accordance with the third embodiment of the present invention, the conformable element 36 may comprise a coating of a conformable material which is applied directly to the outer surface of the catheter body 34, and is preferably selected from the group consisting of wax, silicone rubber, polyurethane, plastic foam, and natural or synthetic rubber. The coating comprising the conformable element 36 is also preferably applied to the catheter body 34 at a thickness of from about 0.002 to 0.005 inches. As an alternative to the coating, the conformable element 36 may comprise a separate sleeve which is positioned on the outer surface of the catheter body 34. Such sleeve has a preferred wall thickness of from about 0.002 to 0.005 inches, and is preferably fabricated from a conformable material selected from the group consisting of polymeric materials and elastomeric materials.

When the delivery catheter 30 is used in conjunction with a self-expanding stent 32 or self-expanding stented graft, the catheter body 34 may also be provided with constraining or latching members 38 which hold or maintain the stent 32 in a rolled or radially compressed configuration about the conformable element 36 until such time as the stent 32 is to be deployed within the desired treatment site. In this respect, the constraining or latching members 38 are retractable from upon the stent 32 to release the stent 32 and allow the stent 32 to unfurl or radially expand to its operative, radially expanded configuration.

As seen in FIG. 9, when the stent 32 is radially compressed or collapsed about the conformable element 36, portions of the conformable element 36 flow upwardly through openings defined within the stent 32, thus causing the stent 32 to be effectively embedded within the conformable element 36.

The use of the delivery catheter 30 occurs in a manner similar to that previously shown and described with respect to the delivery catheter 10, 10a. In this respect, the catheter body 34 of the delivery catheter 30 is advanced through the treatment site of the anatomical passageway such that the stent 32 is operatively positioned within the treatment site. Since the stent 32 is at least partially embedded in the conformable element 36, the stent 32 is prevented from moving or slipping along the catheter body 34 or damaging the luminal surface of the anatomical passageway as the delivery catheter 30 is advanced therethrough. Subsequent to the stent 32 being positioned within the treatment site, the latching members 38 are withdrawn therefrom, thus facilitating the radial expansion of the stent 32 into direct engagement of the luminal surface of the anatomical passageway.

Additional modifications and improvements of the present invention may also be apparent to those of ordinary skill in the art. Thus, the particular combination of parts described and illustrated herein is intended to represent only certain embodiments of the present invention and is not intended to serve as limitations of alternative devices within the spirit and scope of the invention.

What is claimed is:

1. A sheathless delivery catheter for transluminally delivering a radially expandable intraluminal apparatus which is initially mountable upon said delivery catheter in a radially compact configuration, and which is subsequently expandable to a radially expanded configuration for implantation within a mammalian body, said delivery catheter comprising:

an elongate catheter body having a first region upon which said radially expandable apparatus is mountable; and, a conformable material disposed on said first region of said catheter body such that, when said apparatus is mounted in its radially compact configuration upon said first region of the catheter body, said apparatus will form indentations in said conformable material thereby causing said apparatus to become nested within said indentations and at least partially embedded within said conformable material;

said first region of said elongate catheter body being devoid of any surrounding sheath.

2. The delivery catheter of claim 1 for use in conjunction with a self-expanding intraluminal apparatus mountable on said first region of said delivery catheter in its radially compact configuration, wherein said delivery catheter further comprises:

a constraining member for maintaining said self-expanding apparatus in its radially compact configuration, said constraining member being releasable to allow said apparatus to self-expand to its radially expanded configuration.

3. The delivery catheter of claim 1 for use in conjunction with a pressure-expandable intraluminal apparatus mountable on the first region of said delivery catheter in its radially compact configuration, wherein said delivery catheter further comprises:

a pressure-exerting apparatus for causing said intraluminal apparatus to expand from its radially compact configuration to its radially expanded configuration.

4. The delivery catheter of claim 3 wherein said pressure-exerting apparatus is a balloon mounted on said first region of said catheter.

5. The delivery catheter of claim 4 wherein said balloon comprises an inner layer and an outer layer, said outer layer comprising said conformable material.

6. The delivery catheter claim 4 wherein said balloon is fabricated entirely from the conformable material.

7. The delivery catheter of claim 1 wherein said conformable material is selected from the group consisting of:

polyethylene;

polyurethane;

silicone rubber;

natural rubber;

synthetic rubber; and nylon.

8. The delivery catheter of claim 4 wherein said balloon has a wall thickness of about 0.001 to 0.005 inches.

9. The delivery catheter of claim 4 wherein said balloon comprises:

an inner layer fabricated from a non-compliant material; and an outer layer fabricated from said conformable material;

said intraluminal apparatus being at least partially embedded in the outer layer of the balloon when positioned thereupon.

10. The delivery catheter of claim 9 wherein said non-compliant material is selected from the group of materials consisting of:
  polyethylene;
  polyethylene terephthalate; and
  nylon.

11. The delivery catheter of claim 9 wherein said conformable material is selected from the group consisting of:
  polyethylene;
  polyurethane;
  silicone rubber;
  natural rubber;
  synthetic rubber; and
  nylon.

12. The delivery catheter of claim 9 wherein said inner layer has a thickness of from about 0.0001 to 0.0015 inches and said outer layer has a thickness of from about 0.0009 to 0.0035 inches.

13. The delivery catheter of claim 9 wherein said balloon is fabricated via a co-extrusion process to define the inner and outer layers.

14. The delivery catheter of claim 9 wherein said balloon comprises:
  an outer balloon which defines the outer layer; and
  an inner balloon which is disposed within the outer balloon and defines the inner layer.

15. A system comprising the delivery catheter of claim 1 further in combination with a radially-expandable intraluminal apparatus mounted on the first region of said catheter body.

16. The system of claim 15 wherein said intraluminal apparatus is selected from the group of intraluminal apparatus consisting of:
  stent;
  graft; and,
  stented graft.

17. The system of claim 16 wherein said radially expandable apparatus has a plurality of perforations formed therein and wherein said conformable material protrudes through said perforations when said apparatus is mounted thereon in its radially compact configuration.

18. The delivery catheter of claim 4 wherein said catheter body further comprises:
  a balloon inflation lumen through which inflation fluid may be passed into and out of said balloon; and,
  a guide wire lumen which extends longitudinally through which a guidewire may pass such that the catheter may be advanced over a previously inserted guidwire.

19. A delivery catheter for a radially expandable intraluminal apparatus, said delivery catheter comprising:
  an elongate catheter body defining proximal and distal ends and at least one lumen extending longitudinally therethrough;
  an inflatable, expandable balloon disposed on a first region of the catheter body, said balloon having an outer surface; and,
  a conformable material on at least the outer surface of said balloon such that said radially expandable apparatus will at least partially embed in said conformable material when said apparatus is mounted on said first region of the catheter.

20. The delivery catheter of claim 19 wherein said conformable material comprises a coating of a conformable material applied to the balloon.

21. The delivery catheter of claim 19 wherein the conformable material of the coating is selected from the group consisting of:
  wax;
  silicone rubber;
  plastic foam;
  polyurethane;
  natural rubber; and
  synthetic rubber.

22. The delivery catheter of claim 19 wherein said coating is applied to the balloon at a thickness from about 0.002 to 0.005 inches.

23. The delivery catheter of claim 19 wherein said conformable material comprises a sleeve of conformable material positioned upon the balloon.

24. The delivery catheter of claim 23 wherein said sleeve is fabricated from a conformable material selected from the group consisting of:
  polymeric materials;
  elastomeric materials;
  wax;
  silicone rubber;
  plastic foam;
  polyurethane;
  natural rubber; and
  synthetic rubber.

25. A system comprising the delivery catheter of claim 19 further in combination with a radially-expandable intraluminal apparatus mounted on the first region of said catheter body.

26. The system of claim 25 wherein said intraluminal apparatus is selected from the group of intraluminal apparatus consisting of:
  stent;
  graft; and,
  stented graft.

27. The system of claim 25 wherein said radially expandable apparatus has a plurality of open spaces formed therein and wherein said conformable material protrudes through said perforations when said apparatus is mounted thereon in its radially compact configuration.

28. A method of delivering and implanting a radially expandable intraluminal apparatus at a desired location within a mammalian body, said method comprising the steps of:
  (a) providing a delivery/implantation system which includes:
    (1) an elongate catheter body having a distal end;
    (2) an inflatable balloon formed at least partially of a conformable material and disposed on the catheter body at a location proximal to the distal end thereof; and,
    (3) a radially expandable intraluminal apparatus mounted on the balloon in a radially compact configuration and at least partially embedded in the conformable material, said intraluminal apparatus being subsequently radially expandable to a redially expanded configuration;
  (b) inserting a guidewire into the mammalian body;
  (c) advancing the catheter body over the guide wire until the balloon is positioned at the site where the intraluminal apparatus is to be implanted; and
  (d) inflating the balloon to cause said intraluminal apparatus to expand to its radially expanded configuration.

29. A method of delivering and implanting a radially expandable intraluminal apparatus at a desired location within a mammalian body, said method comprising the steps of:

(a) providing a delivery/implantation system which includes:

(1) an elongate catheter body having a distal end;

(2) a conformable material disposed on a first region of the catheter body, said first region being at a location proximal to the distal end of the catheter body;

(3) a radially expandable intraluminal apparatus disposed in a radially compact configuration and mounted on the first region of the catheter body and at least partially embedded in the conformable material, said intraluminal apparatus being subsequently radially expandable to a radially expanded configuration; and, (4) at least one constraining member which is initially engaged with the intraluminal apparatus to hold the apparatus in its radially compact configuration upon said first region of said catheter body, and which is subsequently disengageable from said apparatus to allow said apparatus to self-expand to its redially expand3ed configuration;

(b) inserting a guidewire into the mammalian body;

(c) advancing the catheter body over the guide wire until the first region of the catheter body is positioned at the site where the intraluminal apparatus is to be implanted; and (d) disengaging said at least one constraining member to allow said inraluminal apparatus to self-expand to its radially expanded configuration.

* * * * *